United States Patent [19]

Speidel

[11] 4,090,503
[45] May 23, 1978

[54] SPHYGMOMANOMETER MEASURING CAPILLARY WITH MERCURY SHUT-OFF DEVICE

[76] Inventor: Blasius Speidel, Hochmeisterstr. 33, D 7455 Jungingen, Germany

[21] Appl. No.: 657,248

[22] Filed: Feb. 11, 1976

[51] Int. Cl.² ............................................... A61B 5/02
[52] U.S. Cl. ................................... 128/2.05 G; 73/748
[58] Field of Search ...................... 128/2.05 G, 2.05 R, 128/2.05 U; 73/402

[56] References Cited

U.S. PATENT DOCUMENTS

| | | | |
|---|---|---|---|
| 1,139,519 | 5/1915 | Haseltine | 128/2.05 G |
| 2,011,928 | 8/1935 | Cossor | 73/401 |
| 2,950,621 | 8/1960 | Kallmeyer | 128/2.05 G |
| 3,316,766 | 5/1967 | Jones | 128/2.05 G |
| 3,675,486 | 7/1972 | Speelman | 128/2.05 G |
| 3,855,999 | 12/1974 | Arroyo | 128/2.05 G |

Primary Examiner—William E. Kamm
Attorney, Agent, or Firm—Amster & Rothstein

[57] ABSTRACT

A sphygmomanometer, measuring capillary joined to a mercury storage tank by means of an internal passageway, is provided with a shut-off device for selectively blocking and opening the passageway. The shut-off device has a valve housing including a valve chamber which intersects the passageway and which terminates internally in a valve seat. A locking piece is mounted inside the valve chamber for rectilinear movement, with respect to the valve seat, from a closed position in engagement with the valve seat wherein the passageway is blocked, to an open position removed from the valve seat wherein the passage is open. The locking piece is biased in its open position by means of a spring arrangement, and a lever arrangement including a detenting mechanism is provided to move the locking piece to its closed position and to releasably lock it there.

7 Claims, 9 Drawing Figures

SPHYGMOMANOMETER MEASURING CAPILLARY WITH MERCURY SHUT-OFF DEVICE

The invention relates to a mercury shut-off device for use in a sphygmomanometer with a mercury measuring capillary, with a mercury tank connected thereto via a connecting line in the manner of connected pipes, to which mercury tank a blood pressure rubber bag can be connected and, with a scale bearing the scale values for the measuring capillary, which scale carries the mercury measuring capillary and the mercury tank. The mercury shutoff device which in a first position blocks the connecting line between the mercury measuring capillary and the mercury tank and in a second position opens this connecting line.

With the known sphygmomanometers of this type, the shutoff device is a valve where a conic plug is rotatably located in a housing with a suitable conic bore. The minimum cross section of the passage in the valve plug, which minimum cross section is determined by the connecting line and in most cases is circular, in turn requires a valve plug of relatively large dimensions, particularly at the end with the larger cone diameter. The housing which encloses the valve plug, at least along its conic peripheral surface, has somewhat larger dimensions. As a result, the sphygmomanometers equipped with the known shutoff devices have a correspondingly large space requirement.

The known shutoff devices in the form of valves, because of their design, offer a relatively great resistance to motion. Therefore, the actuating device required for turning the valve plug, which in most cases is a one-arm lever rigidly connected to the valve plug, must be of considerable length, so that the actuating forces acting on the plug may be kept within tolerable limits. Since such an actuating lever, again owing to the design of the valve, ordinarily must be turned by 90° in order to turn the valve plug from the position blocking the connecting line to the position completely opening the connecting line, a large space on the sphygmomanometer must be reserved for the movement of the actuating lever. For this reason, the known sphygmomanometers have a large space requirement necessitating large and therefore heavy containers in which the sphygmomanometers, including their accessories, can be housed and transported. All these factors limit the handiness of the known sphygmomanometers and their possibility of being attached or stored in mounting devices for this special purpose.

It is, therefore, an object of the present invention to provide a mercury shut-off device in a sphygmomanometer, thereby allowing said measuring capillary meter to be more compact than is true of known sphygmomanometers.

This object of the present invention is achieved as follows: The shutoff device provided is a valve comprising within a valve housing a valve seat and a locking piece which is movable rectilinearly in the valve housing along the axis of the valve seat relative to the latter. For a given passage cross section in the open condition, the valve seat and the associated locking piece of such a valve have very small dimensions. The valve housing accommodating the valve seat and the locking piece can be kept small. Since the actuating path for the locking piece also is very small, the space required for the shutoff device and its actuating member is much smaller than with the known sphygomanometers. As a result, the sphygmomanometers and their containers may be much more compact than at present. This benefits their handiness and increases the possibility of sphygmomanometer usage.

In the following, the invention is described by means of an embodiment of a sphygmomanometer shown in the drawings.

Figure 1:
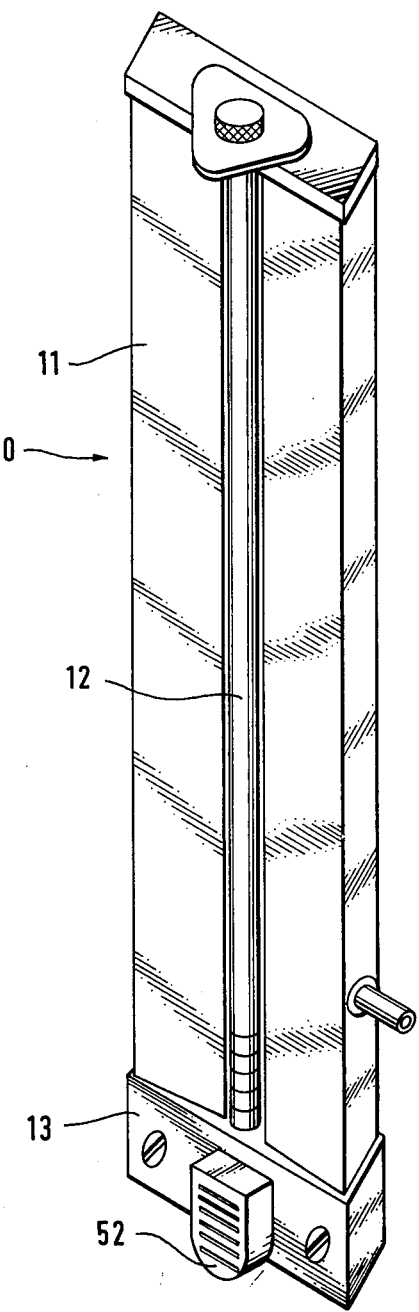
FIG. 1 is a perspective view of an embodiment of a sphygmomanometer in accordance with the present invention, where for better synopsis only the mercury manometer section is shown.

FIG. 1 shows the manometer section of a sphygmomanometer with mercury manometer, designated, generally, as 10. Of its principal assemblies or principal components, FIG. 1 shows only a scale 11, a mercury measuring capillary 12 located on the front side of the scale 11 and a base 13 located at the bottom end of scale 11. Not shown in FIG. 1 is a mercury storage tank located inside the hollow scale 11, a connecting line, contained in base 13, between the mercury storage tank and the measuring capillary, and a shutoff device for the connecting line which shutoff device is also contained in base 13. FIG. 1 also shows part of an actuating lever 52 which is part of an actuating device for the shutoff device. FIG. 1 also shows, at the extreme right of scale 11, a hose connection mounted to the side of scale 11 for connection with the cuff for measuring blood pressure (not shown).

Figure 2:
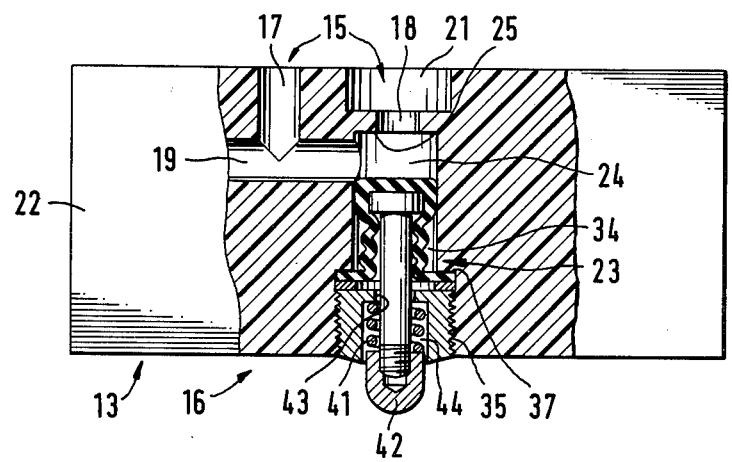
FIGS. 2 and 3 are partial sections and schematic views of a base of the manometer section of FIG. 1 with a shutoff valve in its opened and closed position.
Figure 3:
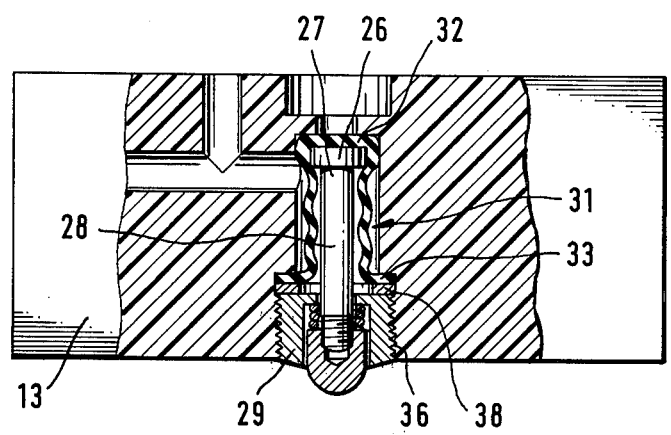

FIGS. 2 and 3 show the design and arrangement of the connecting line 15 between the mercury storage tank and the mercury measuring capillary and the design and arrangement of the shutoff valve 16 which serves as shutoff device for the connecting line. FIG. 2 shows shutoff valve 16 open and FIG. 3 shows it closed.

The connecting line 15 with its line sections 17, 18 and 19 is molded into block-shaped base 13 which is made of synthetic material. The line section 17 is connected to mercury storage tank 81, the upper end of which is shown by the dotted lines of FIG. 1 which is located in the scale 11 (not shown in FIG. 2) and directly adjoins line section 17 in the assembled manometer section. Line section 18 is connected to a depression 21 of circular cross section on the top of base 13. When the manometer section is assembled, this depression 21 holds the bottom end of measuring capillary 12, with a circular gasket in between, so that line section 18 is in direct connection with the measuring capillary 12. The line section 19 provides for cross connection between line sections 17 and 18 which are located apart with their axes parallel to each other.

The shutoff valve 16 as shutoff device is placed between the line sections 18 and 19 of connecting line 15. That part of base 13 which immediately surrounds the shutoff valve 16 constitutes the valve housing 22. This valve housing 22 has a cavity 23 which extends from the outside of valve housing 22 (shown at the bottom of FIGS. 2 and 3) into its inside and has a consistent circular cross section. On the inside end of the cavity 23 is the valve chamber 24 to which line sections 18 and 19 of connecting line 15 are connected. At this inside end of cavity 23, at the end of valve chamber 24, valve seat 25 is located. It is a circular flat seat whose axis coincides with the lengthwise axis of cavity 23. The locking piece 26 of shutoff valve 16 is disk-shaped and placed at end 27, close to valve chamber 24, of a valve stem 28. The valve stem 28 travels via a guide 29 inside cavity 23. A gasket bellows 31 acts jointly with the locking piece 26 and with the valve housing 22 in order to seal the valve chamber 24 from the outside. This gasket bellows 31 is preferably made of a rubber elastic material. In FIGS. 2 and 3, the gasket bellows 31 is shown as a pleated bellows. It may alternately have rounded pleats with the jointly acting parts being modified in accordance with the requirements of a rounded pleated bellows. The end of the gasket bellows 31, which is connected to locking piece 26, has the form of a closed cap 32, which completely covers the locking piece 26 along its peripheral surface on the side facing the valve seat 25. As a result, because of its elasticity, the cap 32 of gasket bellows 31 acts as gasket for the shutoff valve 16 in the closed position shown in FIG. 3. The end of gasket bellows 31, facing away from cap 32, is provided with an annular flange 33.

The cavity 23 has two successive sections 34 and 35 placed axially, of which section 34, which is closer to the inside, acts at its inside end as valve chamber 24. The outside section 35 is provided with a thread 36 into which guide 29, which has a corresponding thread for the valve stem 28, is threaded. The outside section 35 of cavity 23 has a larger outside diameter than the inside section 34. A plane annular ledge 37 is located between these two cavity sections. On this ledge 37 is that part of gasket bellows 31 which acts jointly with valve housing 22—namely its annular flange 33—and is clamped by means of guide 29, with a spacer 38. This results in hermetic sealing off of valve chamber 24 from the outside.

The shutoff valve 16 is equipped with a valve spring 41 which is a helical compression spring. It is located on that part of valve stem 28, which projects from guide 29. One end of valve spring 41 is supported by guide 29 and the other end is supported by a spring retainer connected to valve stem 28. This spring retainer has the form of an end cap 42 with a rounded end surface. The end cap 42 is threaded to that end of valve stem 28 which faces away from the locking piece. In order to keep the height of shutoff valve 16 as low as possible, guide 29, on the side facing away from locking piece 26, has a recess 44 which is flush with the guide surface 43 for the valve stem 28. This recess has a circular cross-section and a diameter which is greater than the outside diameter of valve spring 41. The depth of recess 44 is slightly greater than the length of valve spring 41 located between the bottom of recess 44 and the end cap 42; as a result, the annular front surface of end cap 42, which constitutes the spring retainer for valve spring 41, dips slightly into recess 44 and hence prevents this front surface from coming into contact with the edge of the recess.

The locking piece 26, under the action of valve spring 41, is in its rest position in which the connecting line 15 is open. In order to move locking piece 26 to the position closing the connecting line, as shown in FIG. 3, there is provided an actuating device 51 which will be explained in detail below by means of FIGS. 4 - 9.

The principal component of actuating device 51 is an actuating lever 52 which is a single-armed lever. It is pivotable on valve housing 22 by means of a pivot bearing 53 which is located on the valve housing in that cross-sectional plane which passes through the longitudinal axis of cavity 23 and hence of the shutoff valve 16, and is denoted in FIG. 5 by the dot-dash line 57. This cross-sectional plane also constitutes the plane of motion of actuating lever 52 so that the end cap 42, which is connected to locking piece 26 via valve stem 28 and projects from the valve housing 22, is located in the plane of motion of actuating lever 52.

Figure 4:
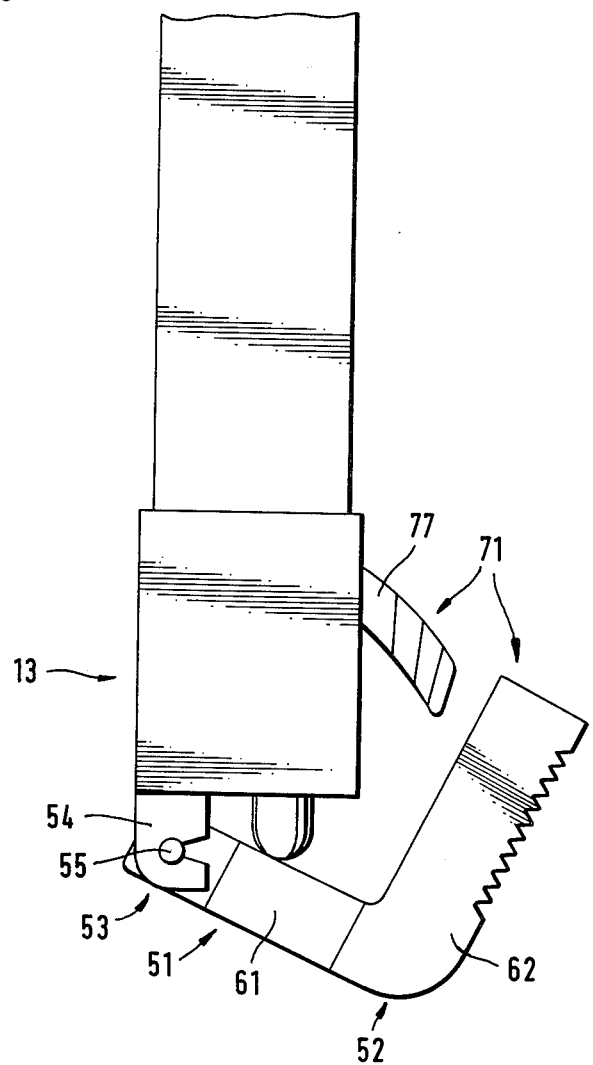
FIG. 4 is an enlarged partial sideview of the manometer section of FIG. 1.
Figure 9:
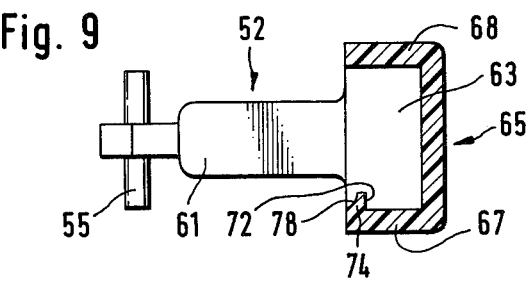
FIG. 9 is a top view, partially sectioned along line 9—9 in FIG. 8, of the actuating lever.
Figure 7:
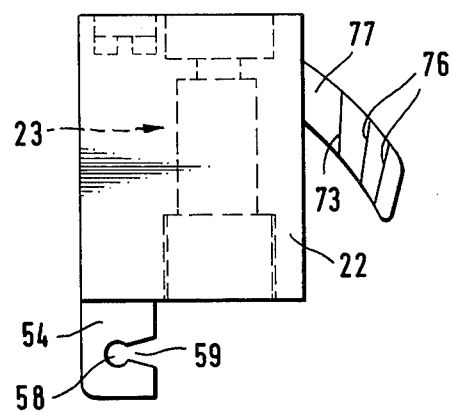
FIG. 7 is a sideview of the base of the manometer section.

As indicated in FIGS. 4 and 7, the fork-shaped bearing block is located on the underside of the block-shaped base 13 enclosing the valve housing 22, and is directly adjacent to that edge which is furthest from the central axis of the shut-off valve. The two cheeks of bearing block 54 have an aligning passageway. In a longitudinal section plane parallel to the underside of base 13, the cheeks of bearing block 54 have a cut-out 59 extending from the wall of the passageway to the outside. The walls of cut-out 59 are inclined outward from the wall of passageway 58, symmetrically to the bisecting plane, until their distance is greater than the outside diameter of pivoting trunnion 55. The narrow passage of cut-out 59, which is located at the point of transition to the peripheral wall of passageway 58, has an inside diameter which is smaller than the outside diameter of pivoting trunnion 55 and, in accordance with the material and form elasticity of cheeks 54, is designed so that the pivoting trunnion 55 can be forced through this narrow passage while elastically spreading the boundary walls of cut-out 59 till it snaps into passageways 58. Because of this design of the cheeks of the bearing block, the pivoting trunnion can be located rigidly in passageway 56 at the end of actuating lever 52 as shown in FIG. 9. For this purpose, a pivoting trunnion 55, made of metal, can be mounted in passageway 56, or, perhaps, may be molded as part of the actuating lever 52 which is molded from a synthetic material. A pivoting trunnion 55, made of thermoplastic material, can be tip-stretched to the actuating lever 52 during its manufacture directly to form two aligned sections of circular cylindrical shape. At any rate, this prevents the pivoting trunnion 55 from being lost.

Figure 8:
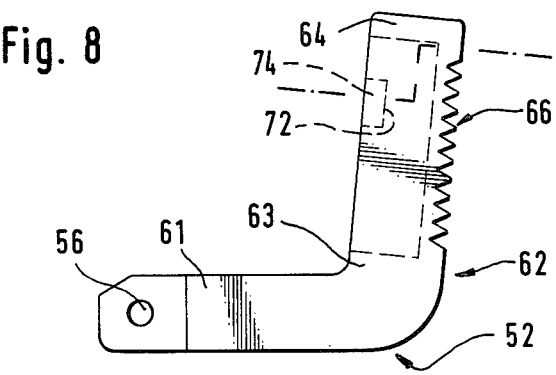
FIG. 8 is a sideview of an actuating lever for the shutoff device in the base of the manometer section of FIG. 1.

As shown in FIGS. 4 and 8, actuating lever 52 has approximately a right angle bend in the center of its length and within its plane of motion defined by its pivot bearing 53. The length of rectilinear part 61, extending from pivot bearing 53, is approximately equal to or only slightly larger than the distance of the axis of pivot bearing 53 from that edge of base 13 to which actuating lever 52 extends. This rectilinear section 61 has an approximately square cross-section outside the region of the cheeks of the bearing block 54. The angled section 62 of actuating lever 52 has a U-shaped cross-section profile (see FIG. 9) whose two legs, 67 and 68, are parallel to the plane of motion of actuating lever 52, and face valve housing 22. Owing to two cross walls 63 and 64, closing the U-profile at its two front sides, the angled section 62 of actuating lever 52 is box-shaped with an open side facing valve housing 22. This box-shaped angled section 62 of actuating lever 52, with its outside, forms a type of actuating plate 65 which is in the form of a finger-operated switch and whose surface is equipped with a knurling pattern 66.

As is clearly indicated in FIG. 1, the angular design of actuating lever 52 permits the latter to conform closely to the base 13. As a result, the actuating lever 52 requires very little space and this facilitates the attachment of the manometer section 10 to the most varied supports or the most varied containers. With a shut-off valve where the locking piece is not under the action of a valve spring, the locking piece, or a solidly connected part thereof, is linked to the actuating lever (if required with interposition of additional links) so that the locking piece can be moved by the actuating lever from one valve position to the other and vice versa. With the embodiment shown the valve spring 41 forces the end cap 42, which is solidly connected to locking piece 26, out of valve housing 22. Hence mere contact of the end cap with the actuating lever is sufficient to engage actuating lever 52. In order to hold the locking piece 26 in its position blocking the connecting line 15, a detaining device is required which acts jointly with the actuating lever and by which the actuating lever can be detented in the detent position against the force of valve spring 41.

The detenting device 71 described below by FIGS. 4 and 6-9 has two plane detent surfaces 72 and 73. Of these two detent surfaces, the first detent surface 72 is located on actuating lever 52 and is part of a detent catch 74 which is located on leg 67 of the U-profile of the angled part 62 on the interior of the profile. The surface normal of the first detent surface 72 is aligned, at least approximately, with the tangent of its path of motion and, in addition, in the detent position of actuating lever 52, is directed in the same direction as its direction of motion towards its rest position. The second detent surface 73 is part of a detent catch 75, which is located on a projection 77 of valve housing 22 and is thus connected thereto. The detent catch 75 is located in such a way that its detent surface 73, in the detent position of actuating lever 52, projects, at least partially, into the path of motion of that lever's detent surface 72, with the surface normal of the second detent surface 73 being nearly parallel to the surface normal of the first detent surface and in a direction opposite thereto.

The projection 77, connected to the valve housing 22 and which bears detent catch 73, is curved along a circular arc which is located in the plane parallel to the plane of motion of actuation lever 52 and whose center is aligned with the axis of pivot bearing 53. As seen from valve housing 22, projection 77, beyond detent surface 73, has two additional detent surfaces 76 on suitably designed detent catches. These additional detent surfaces 76 are only provided for safety's sake, e.g., for those cases of manometer 10 use, where an unintentional loosening of the detent device must be expected owing to vibrations or other external forces. However, in most cases of use, they can be dispensed with since their absence rather insures that the detent surface 72 on actuating lever 52 actually detents in the detent surface 73 which determines the closed position of locking piece 26.

Both the detent catch 74 on actuating lever 72 and the detent catch 75 on projection 77, on the sides facing away from their respective detent surfaces 72 or 73, have a starting ramp 78 or 79; the starting ramp 79 of detent catch 75 is located in the plane of motion of starting ramp 78 of detent catch 74 on actuating lever 52 and both starting ramps 78 and 79 at their juncture, are at least nearly parallel to each other.

The detent process is facilitated by the elasticity, present at right angles to the plane of motion of actuating member 52, of actuating lever 52 and projection 77. Furthermore, the actuating lever 52, owing both to its relatively great length and the resulting relatively large distance of detent catch 74 from pivot bearing 53, and to the spring-like clamping of its bearing trunnions 55 in the passageways 58 which are laterally open owing to the cut-out 59, has a sufficiently large elastic lateral mobility or deformability normal to its plane of motion so that its detent surface 72 can be easily made to disengage from detent surface 73.

Figure 5:
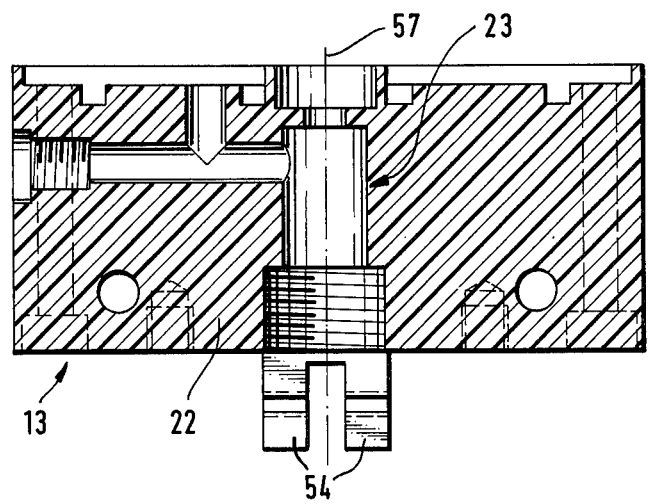
FIG. 5 is a lengthwise section of the base of the manometer section of FIG. 1.
Figure 6:
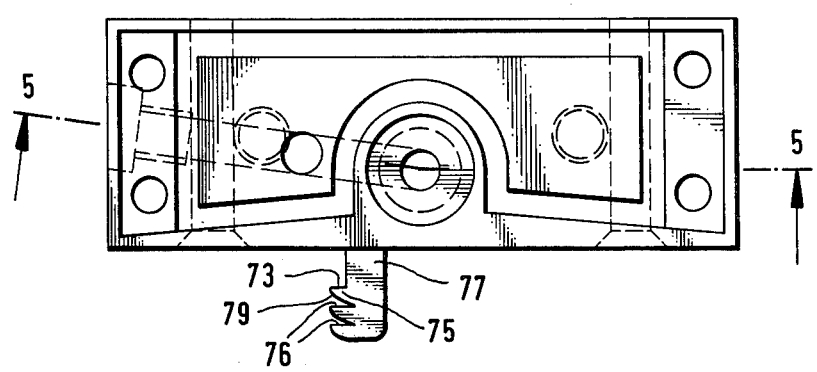
FIG. 6 is a top view of the base of the manometer section.

As is evident in FIGS. 2 and 3 in conjunction with FIGS. 5-7, the valve housing 22 is connected with depression 21 which forms a recess for the measuring capillary 12 and the axis of valve seat 25 is aligned with the axis of measuring capillary 12. As a result, and because of the relatively small outside diameter of shut-off valve 16, its accommodation requires no greater dimensions than those already required by the presence of the measuring capillary. Because the base 13 enclosing the valve housing 22 can be formed, in a manner not shown, as the lower end wall of the mercury storage tank, which is a cavity, open downward, of the lower part of scale 11, and because the valve housing contains the connecting line 15 between the mercury storage tank and the measuring capillary, and because this requires minimum dimensions, there has been created a sphygmomanometer with a very compact manometer section which, owing to its small space requirement, can be more easily attached than previously, to special supports or can be more easily accommodated in containers. Vice versa, with the same space requirement, these supports, or containers, can be made smaller and, therefore, lighter.

Although a specific embodiment of the invention has been disclosed for illustrative purposes, it will be appreciated by one skilled in the art that various modifications, additions, and substitutions are possible without departing from the scope and spirit of the invention.

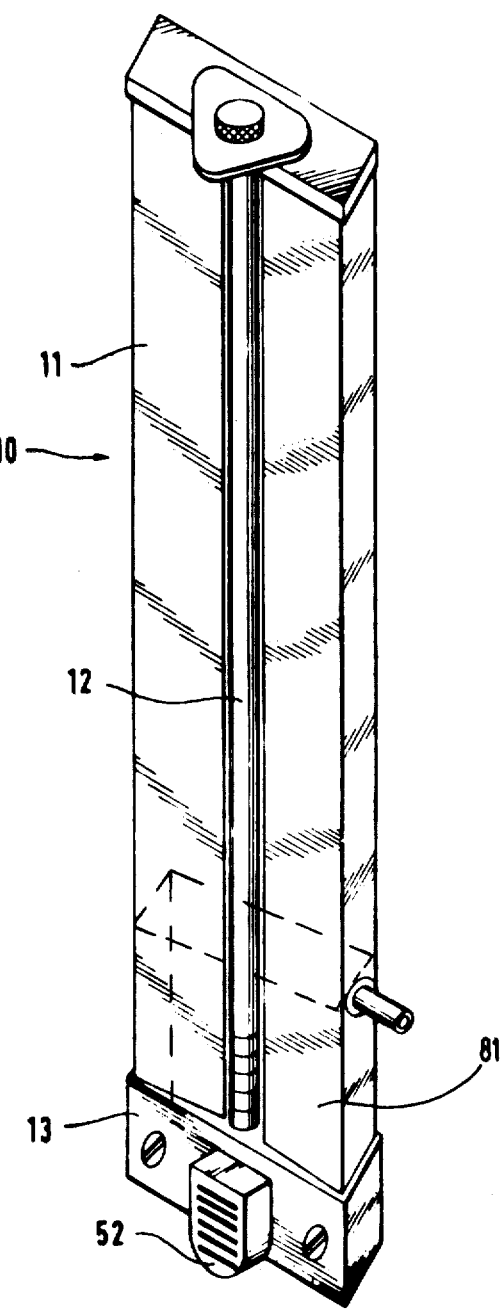

What is claimed is:

1. In a sphygmomanometer including a mercury measuring capillary connected to a mercury storage tank by means of a passageway in said sphygmomanometer, a shut-off device operative selectively to block and open said passageway, comprising: a valve housing including a valve chamber intersecting said passageway; a valve including a valve stem and a locking piece and mounted within said valve chamber for movement between a first position and a second position; and a bellows gasket having a first end affixed to one of said locking piece and said valve stem, and a second end connected to said valve housing, said bellows gasket serving to seal off said valve chamber from the remainder of said passageway when said valve is in said first position.

2. In a sphygmomanometer including a mercury measuring capillary connected to a mercury storage tank through a passageway in said sphygmomanometer, a shut-off device operative to selectively block and open said passageway, comprising:

a valve housing having a generally cylindrical internal cavity extending axially to the exterior of said housing and including an outer portion, and an inner portion of reduced diameter defining a valve chamber which intersects said passageway, the innermost end of said valve chamber serving as a valve seat, the juncture between said inner and outer portions including an annular rim resulting from the reduction in diameter;

a generally disc-shaped locking piece having a valve stem concentrically affixed to a first surface thereof and extending axially within said cavity towards the exterior of said housing, said locking piece being mounted for rectilinear movement along the axis of said valve chamber between a first position for blocking said passageway and a second position for opening said passageway;

a generally cylindrical bellows gasket having a closed end secured to the second surface of said locking piece and an open end engaging said rim; and a valve stem guide mounted in the outer portion of said cavity to clamp said gasket against said rim, said valve stem guide having an aperture therein constructed to permit said valve stem to slide freely therethrough so that rectilinear motion can be imparted to said locking piece.

3. The sphygmomanometer according to claim 2 wherein said valve stem guide includes a recess extending inwardly from the exterior of said valve housing, said sphygmomanometer further comprising:

a spring retainer secured at the free end of said valve stem; and a helical compression spring coaxially mounted on said valve stem within said recess between said spring retainer and the innermost surface of said recess, said spring providing a force to withdraw said locking piece from said valve seat.

4. The sphygmomanometer according to claim 2 further comprising:

an actuating lever mounted for pivotal movement with respect to said valve housing; and means coupling said actuating lever to said locking piece so that the pivotal movement of said actuating lever is converted to rectilinear movement of said locking piece between said first and second positions.

5. The sphygmomanometer according to claim 4 further comprising:

resilient means constructed and arranged to apply a force for moving said locking piece to one of said first and second positions; and detenting means for releasably locking said actuating lever in a detent position against the action of said resilient means.

6. The sphygmomanometer according to claim 5 wherein said actuating lever is mounted for pivotal movement with respect to a first surface of said valve housing and at least a portion of said detenting means is mounted to a second surface of said valve housing sharing a common edge with said first valve housing surface, said actuating lever being angled around said common edge by approximately the same angle subtended by said first and second housing surfaces.

7. The sphygmomanometer according to claim 5 wherein said detenting means comprises:

a detent catch on said housing having a detent surface facing towards the interior of said housing;

a detent catch on said actuating lever positioned to interfere with said housing detent catch when said actuating lever is moved and having a detent surface facing away from said housing;

at least one of said detent catches being movable in a direction lateral to the direction of movement of said actuating lever, at least one of said detent catches having a ramp surface facing away from its detent surface and arranged to impart lateral movement to said at least one laterally movable detent catch when said actuating lever is moved, so that said detent catches are permitted to slip past each other to bring said detent surfaces in confronting relationship, whereby said actuating lever is releasably locked in its detent position.

* * * * *

UNITED STATES PATENT OFFICE
CERTIFICATE OF CORRECTION

Patent No. 4,090,503　　　　　　　　　Dated May 23, 1978

Inventor(s) Blasius Speidel

It is certified that error appears in the above-identified patent and that said Letters Patent are hereby corrected as shown below:

In the drawing, Figure 1 should appear as shown on the attached sheet.

Signed and Sealed this

Thirteenth Day of March 1979

[SEAL]

Attest:

RUTH C. MASON
*Attesting Officer*

DONALD W. BANNER
*Commissioner of Patents and Trademarks*